(12) United States Patent  (10) Patent No.: US 7,426,258 B1
Zweig  (45) Date of Patent: Sep. 16, 2008

(54) HIGH RESOLUTION LOW DOSE MAGNIFYING X-RAY FLUOROSCOPE AND SYSTEM

(75) Inventor: Gilbert Zweig, Morris Plains, NJ (US)

(73) Assignee: Glenbrook Technologies, Inc., Randolph, NJ (US)

( * ) Notice: Subject to any disclaimer, the term of this patent is extended or adjusted under 35 U.S.C. 154(b) by 0 days.

(21) Appl. No.: 11/606,453

(22) Filed: Nov. 30, 2006

(51) Int. Cl.
*H05G 1/64* (2006.01)
(52) U.S. Cl. ..................................... 378/98.3
(58) Field of Classification Search ............. 378/42, 378/62, 91, 98, 98.2, 98.8, 116, 189, 190; 250/370.08, 370.09, 370.11; 600/407, 425, 600/427
See application file for complete search history.

(56) References Cited

U.S. PATENT DOCUMENTS

2002/0196899 A1*  12/2002  Karellas .................... 378/98.8

* cited by examiner

*Primary Examiner*—Courtney Thomas
(74) *Attorney, Agent, or Firm*—Michael R. Philips

(57) ABSTRACT

A high resolution magnifying X-ray fluoroscope using a low dose beam includes a scintillator for receiving an X-ray beam and converting the X-ray energy into visible light. The scintillator is in intimate optical contact with a non-demagnifying image intensifier that presents the visible light image through a close-up lens system to an optically magnifying, autofocus, programmable, closed circuit video camera. The fluoroscope is mounted on a moveable frame in a position that is opposed to an X-ray source.

16 Claims, 5 Drawing Sheets

HIGH RESOLUTION LOW DOSE MAGNIFYING X-RAY FLUOROSCOPE AND SYSTEM

FIELD OF THE INVENTION

The present invention relates to the field of real-time fluoroscopic X-ray imaging, and more particularly to fluoroscopic X-ray imaging at high resolution generated through the use of low dose X-ray beams.

BACKGROUND OF THE INVENTION

Conventional real-time fluoroscopic X-ray imaging involves directing an X-ray beam through an object to impinge onto a scintillator that converts the X-rays into energy in the visible spectrum. The scintillator is typically a layer of luminescent or phosphorescent material that is capable of generating visible light in response to being stimulated by the X-ray beam. When the X-ray beam passes through portions of the object under examination that are opaque to varying degrees to X-ray wavelengths, e.g. bone or metal, a shadow defining the configuration and position of the opaque portion is formed. The resultant visible light shadow is then typically intensified and reduced in size prior to being transmitted by video means, observed by a technician, and/or recorded. Intensification is conventionally achieved by use of a cesium iodide scintilator demagnifying intensifier tube. Conventional fluoroscopic X-ray imaging systems are used commonly for medical, security and industrial applications.

Systems have been developed for converting the X-ray shadow image to a digital signal to conveniently display or record the image or to transmit the image via television. These digital systems commonly utilize a flat panel detector, essentially a planar array of photosensors or CCDs (charge coupled devices) connected to electronic apparatus. One such system is disclosed in U.S. Pat. No. 6,895,077 entitled SYSTEM AND METHOD FOR X-RAY FLUOROSCOPIC IMAGING. The visible light beam created in the scintillator projects to a portion of the array to activate a photosensor receptor that is connected to an output cable. The sum of all the photosensor receptors equates to a total screen picture. To create a moving image, as is common in fluoroscopic imaging for observing internal organs or guiding arthroscopic surgery, the array of photosensors receives a changing image over time and transmits sequential panels of information. As a result, the digital flat panel is analogous to $20^{th}$ century motion picture technology in which an individual frame was exposed, then the film advanced to expose a subsequent frame. By exposing many frames in succession, a live-appearing sequence, or motion picture, was created. Standard motion picture speed captures and displays at a rate of at least 16 frames per second to achieve a realistic motion sequence. In the flat panel X-ray system, a maximum image capture rate of 10 frames per second can be achieved. This capture rate, based on photosensor-digital technology, is insufficient to approach real-time motion viewing that is needed to accurately explore an object or guide an operative procedure. Thus the use of digital imaging is not effective and it is essential to transmit the image in analog format to achieve real-time quality. Digital flat panel imaging devices are neither real-time (i.e. fluoroscopic) nor high resolution (less than 7 lp/mm).

As with all imaging formats, image sharpness is a major concern. In the case of visible spectrum converted X-ray imaging, whether medical, security, or industrial, image resolution can be crucial. Image resolution is defined in units of line pairs (a line and a space) per millimeter (lp/mm), that is, the maximum number of line pairs that can be observed in a millimeter of width and distinguished as separate lines. In other words, resolution determines the smallest distinguishable white space between two parallel lines. Prior fluoroscopic X-ray image systems have achieved resolution of up to 5 lp/mm. For acceptable clarity, a resolution of at least 12 lp/mm is needed to visualize small details and comprehend their importance. For example, an X-ray examination of an implanted vascular stent must be sufficiently clear to identify minute problems that occasionally occur. Simply magnifying a small image that is of low resolution will merely provide an unclear larger image. Reducing the size of a large image to intensify the pattern also fails to achieve detail clarity. Early fluoroscopic systems included a scintillator that projected visible light energy to a demagnifying image intensifier which transmitted a smaller image to a camera device. These systems use unacceptably high X-ray dosage, and deliver relatively poor image resolution, on the order of 5 lp/mm or less.

Image resolution could, theoretically, be enhanced by increasing the intensity or dose of the X-ray beam. However, an increased dose X-ray beam has serious physiological implications both for the patient being examined fluoroscopically and for the medical technician. Thus it is important to reduce X-ray dosage as much as possible. The U.S. Food And Drug Administration monitors radiation relating to the use of fluoroscopic guidance of minimally invasive internal procedures, e.g. angioplasty. The FDA guidelines list time exposures of X-rays that have been shown to cause skin damage resulting from a dose of 2.0 Rads/minute. Longer time at a given radiation dose can cause greater damage, both to the skin and to internal organs. Lower dose rates are deemed to be safer.

Therefore, a need exists for a high resolution fluoroscopic X-ray system capable of magnified real-time motion perception and generated from use of a low dose X-ray beam. The invention disclosed below provides such an X-ray fluoroscope.

SUMMARY OF THE INVENTION

The high resolution real-time X-ray image fluoroscope and system of the present invention includes an X-ray source for penetrating an object with an X-ray beam that is received in a fluoroscope. The X-ray source and fluoroscope are mounted opposite one another on a moveable frame. The fluoroscope has a radioluminescent scintillator optically coupled to a non-demagnifying image intensifier. The intensified image is viewed via a close-up lens device to be focused onto an autofocusing, optically magnifying camera. The closed circuit camera transmits the high resolution, magnified video image to a computer or other viewing or recording device.

BRIEF DESCRIPTION OF THE DRAWINGS

The present invention is best understood in conjunction with the accompanying drawing figures in which like elements are identified by similar reference numerals and wherein.

DETAILED DESCRIPTION OF THE PREFERRED EMBODIMENT

Figure 1:
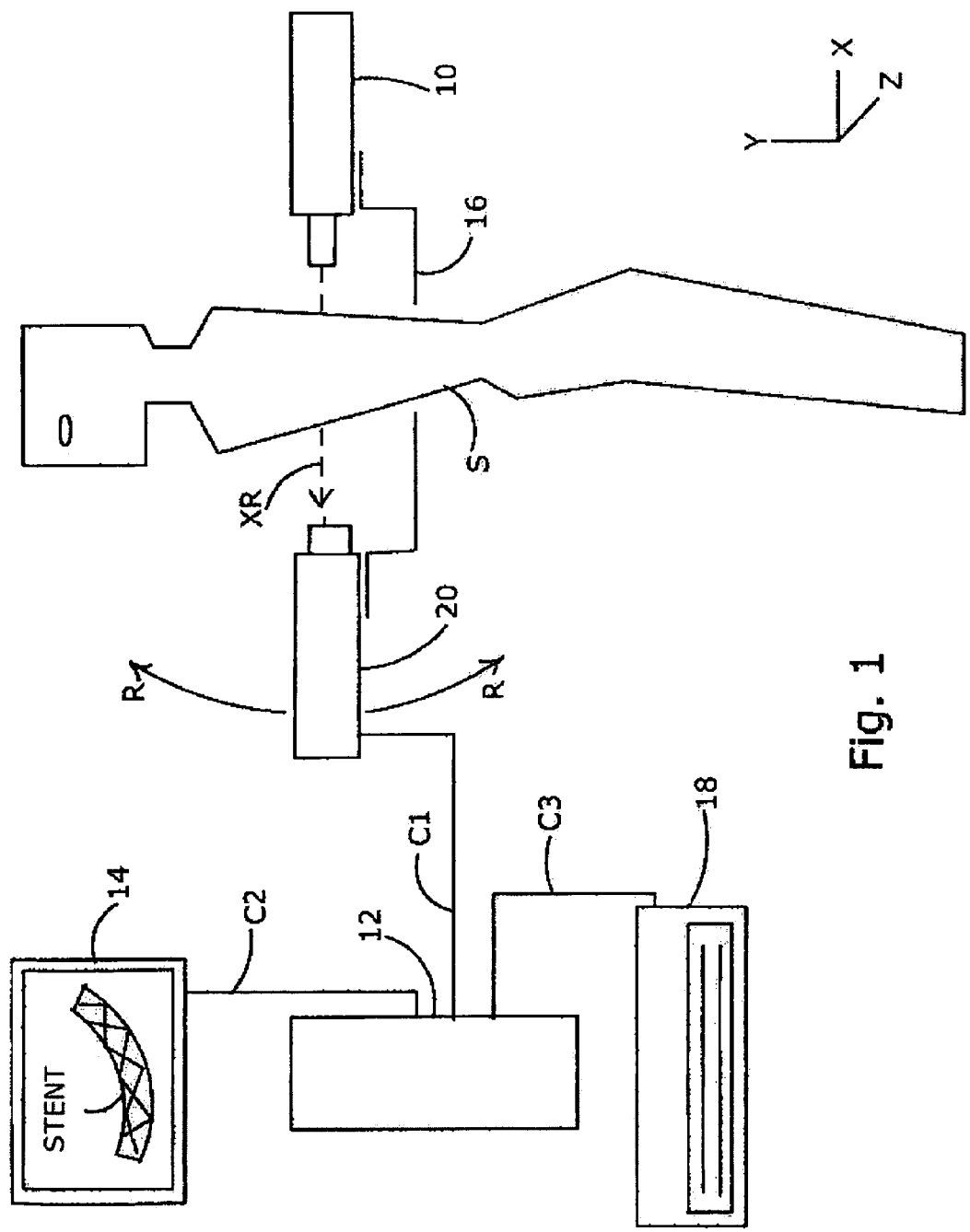
FIG. 1 is a diagrammatic side view of the high resolution real-time fluoroscopic X-ray imaging system of the invention in use.

Referring now to FIG. 1, a schematic side elevation view is illustrated of the high resolution, magnifying X-ray fluoroscopic imaging system according to the invention. A subject S is positioned between an X-ray source 10 and a fluoroscope 20 in the path of an X-ray beam XR. X-ray source 10 and fluoroscope 20 are mounted on a common frame 16 to maintain alignment therebetween. X-ray source 10 is a substantially conventional generator and projector of an X-ray beam as is known in the field. X-ray fluoroscope 20 will be described in detail below. Frame 16 is structurally rigid and mounted in a manner to be moveable in the Y and Z directions (see diagram at bottom right) either manually or mechanically. Movement of frame 16, and resultant movement of X-ray source 10 and X-ray imaging fluoroscope 20, enables a scanning image of an area of subject S, for example to inspect in real-time the condition of and around an implanted object in subject S, e.g. a vascular stent. The real-time inspection of implanted objects such as stents and imaging of surgical procedures such as catheterization, stent deployment, etc. are major benefits of the present invention. As used herein, real-time involves displaying image movement substantially synchronously with object or camera movement. Frame 16 is additionally able to be rotated in the direction indicated by arrows R around an axis midway between X-ray source 10 and X-ray fluoroscope 20 to inspect an area of subject S at an angle to horizontal. X-ray beam XR from X-ray source 10 passes through subject S and enters X-ray fluoroscope 20 where it is first converted to visible light, intensified without demagnification, optically magnified, and converted to an autofocus video image to exit through a cable C1 to enter a signal processor, e.g. CPU 12. In passing through subject S in a location for imaging in real-time a surgical procedure or implanted object, portions of X-ray beam XR are absorbed or blocked by opaque objects, e.g. bones or a dense implant, and other portions of X-ray beam XR pass through translucent portions, creating a shadow image that depicts the shape of the opaque portions. CPU 12 transmits an image via cable C2 to display 14 or an image recording device (not shown) similarly connected. Display 14 may be located close to X-ray fluoroscope 20 or remote therefrom. Power input to the various operating components of the system is not depicted and understood to be according to the requirements of the individual component. An operator interface 18, e.g. a keyboard, is connected to CPU 12 via cable C3 for control of the positioning of frame 16 and the functioning of X-ray source 10 and fluoroscope 20. An image of a stent is portrayed on display 14 as an implanted object in the body of subject S requiring occasional non-invasive evaluation with high resolution and clarity.

Figure 2:
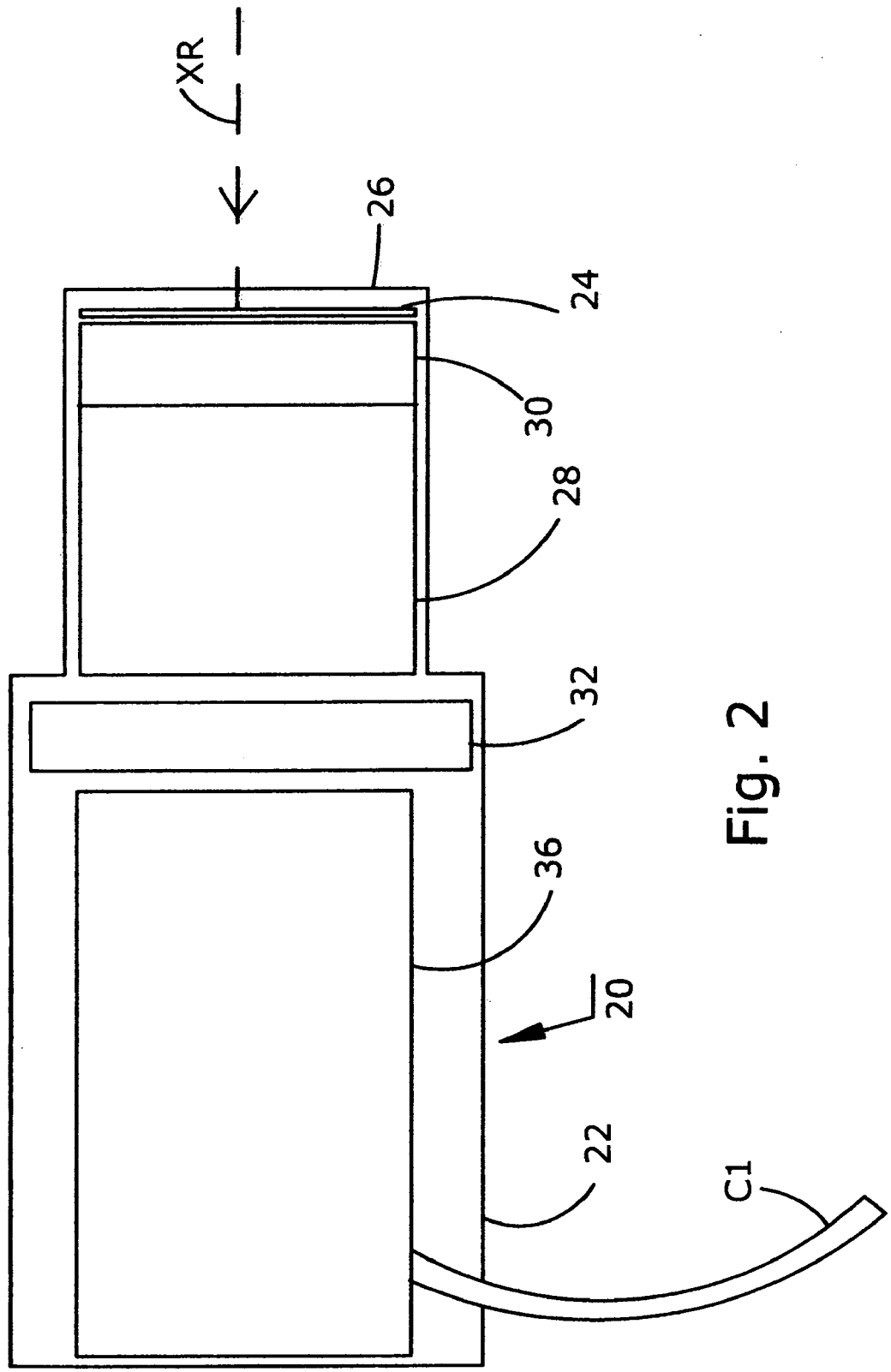
FIG. 2 is a diagrammatic side view of the X-ray fluoroscope according to a preferred embodiment of the invention.

Referring now to FIG. 2, X-ray fluoroscope 20 is depicted schematically to show internal components in detail. A housing 22 encloses and supports the components comprising X-ray fluoroscope 20. At least the window portion 26 of housing 22 is transparent to X-ray. X-ray beam XR passes through window portion 26 to impinge on scintillator 24, being in the form of a thin sheet or coating of radioluminescent phosphor, for example CsI or $Gd_2O_2S$. Scintillator 24 converts the impinging X-ray input radiation frequency into a visible light frequency for further processing and image projection. Scintillator 24 is positioned and maintained in intimate optical contact with the input end of a non-demagnifying image intensifier 28 to maximize transmission integrity. Scintillator 24 may be formed by directly depositing the selected phosphor on the input of image intensifier 28 or by adhering a formed phosphor sheet scintillator to the image intensifier input. Alternatively, a phosphor is deposited, or a phosphor sheet is adhered, onto a fiber optic plate or taper 30 that is in intimate optical contact with image intensifier 28. Image intensifier 28 is of the type able to increase the energy of visible light transmitted therethrough by electronic or electrostatic means while maintaining a constant image size. A specific type of non-demagnifying image intensifier that is satisfactory to the objects of the invention is known as a microchannel plate, characteristically a thin plate of conductive glass with a large number of very small apertures, on the order of 10 µm in diameter. The apertures, or microchannels, are coated to cause a single incoming light ray impacting the side wall to divide multiple times, adding photons and thus intensifying the energy level of the light ray projected therefrom. An available non-demagnifying microchannel plate image intensifier is capable of projecting an image with a resolution on the order of 25-28 lp/mm.

Referring further to FIG. 2, the intensified, non-demagnified image next passes through a close-up lens system 32 capable of focusing and transmitting the image received from proximally located image intensifier 28 to a camera 36. Camera 36 generates a video signal representing the image which is transmitted via cable C1 to an output device. Camera 36 is a compact programmable, autofocus block camera having an optical magnification multiplier of 10× and a digital zoom of 4×, equal to a total magnification capability of 40×. It is noted that optical magnification retains details and clarity to attain a desired level of resolution. A camera adequate to the requirements of the present invention is Model FCB-1X Series by Sony Corporation.

Figure 3:
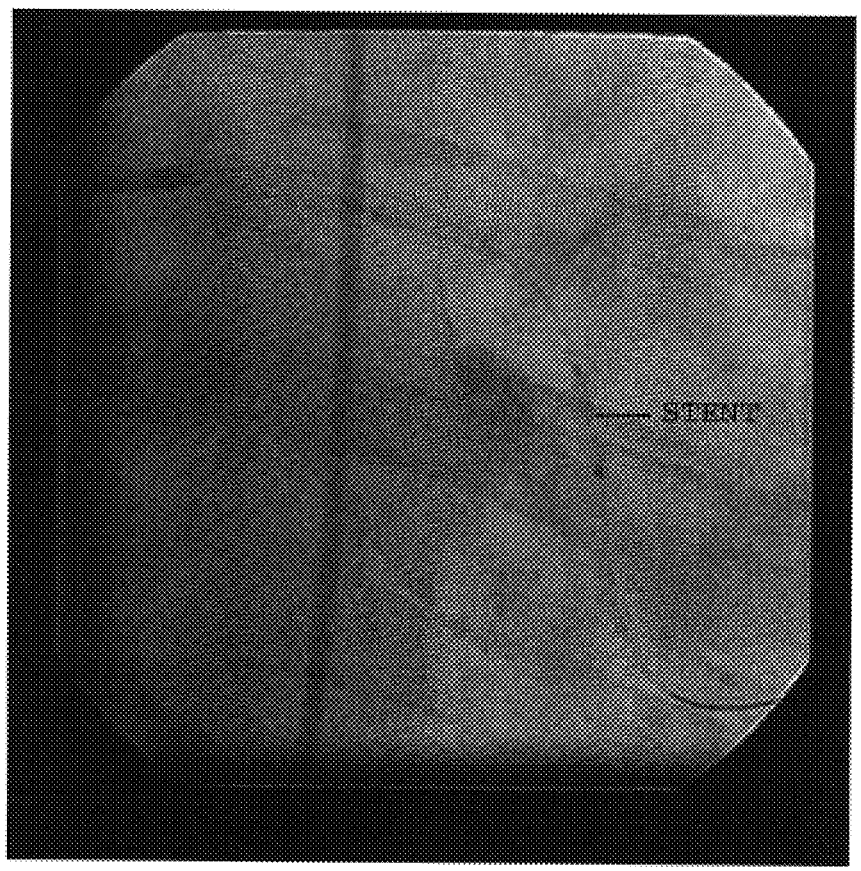
FIG. 3 is a fluoroscopic image of a stent obtained under clinical conditions of angiography, using conventional X-ray fluoroscopy of the prior art.

Referring now to FIG. 3, a fluoroscopic image of an implanted stent as viewed through a human subject chest is shown as a typical example of results achieved using fluoroscopic equipment known in the prior art. The stent is barely discernible, but no details are perceptible. The X-ray dose employed to obtain this fluoroscopic image is in the range of 2000 mRad/minute, a potentially toxic dose.

Figure 4:
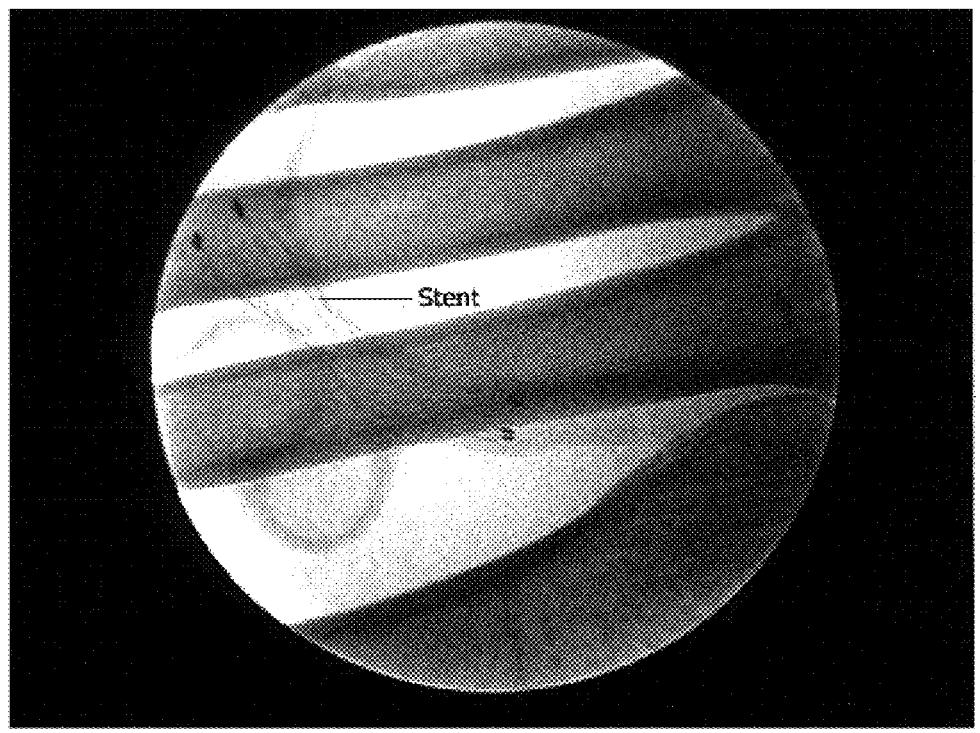
FIG. 4 is a fluoroscopic image of a stent through a human bone foot phantom as derived from a fluoroscope according to the present invention.

Referring now to FIG. 4, a fluoroscopic image of a stent viewed by use of the invention X-ray fluoroscope through a human foot phantom is shown. A foot phantom is a model foot for use in evaluating X-ray equipment and methods. The stent appears well defined. The X-ray dose used is only 10 mRad/hour, or 0.17 mRad/minute, significantly less than the dose rate delivered when using the prior art equipment.

Figure 5:
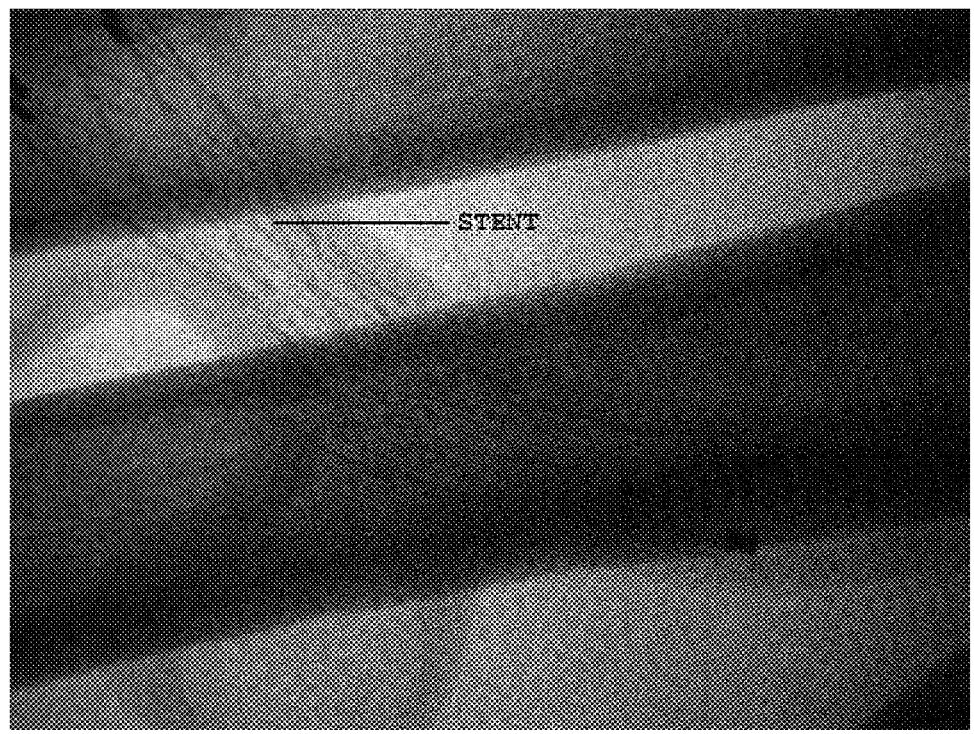
FIG. 5 is a fluoroscope optically magnified view of the stent of FIG. 4 as derived from a fluoroscope according to the present invention.

The fluoroscopic image shown in FIG. 5 is the result of magnifying the image of FIG. 4. In FIG. 5, the stent is clearly displayed large enough to determine any problem areas by visual examination. This degree of detail and magnification clearly indicates a highly resolved image.

While the description above discloses preferred embodiments of the present invention, it is contemplated that numerous variations of the invention are possible and are considered to be within the scope of the claims that follow.

What is claimed is:

1. A high resolution low dose magnifying X-ray fluoroscope for real-time motion imaging, comprising:
   a. a scintillator positioned to receive an X-ray beam that has passed through an object, the scintillator converting the X-ray beam into a visible light image;

b. a non-demagnifying image intensifier in intimate optical contact with the scintillator for intensifying the visible light image; and c. a closed circuit video camera having optical magnification and autofocus capabilities mounted adjacent to the image intensifier.

2. The high resolution magnifying X-ray fluoroscope described in claim 1, further comprising a close-up lens system mounted proximally between the image intensifier and the camera.

3. The high resolution X-ray fluoroscope described in claim 1, wherein the scintillator comprises a phosphor coating deposited on an input of the image intensifier.

4. The high resolution X-ray fluoroscope described in claim 1, further comprising a fiber optic component optically coupled to an input of the image intensifier and wherein the scintillator comprises a phosphor coating on the fiber optic component.

5. The high resolution X-ray fluoroscope described in claim 2, wherein the close-up lens system is optically coupled to the camera.

6. The high resolution X-ray fluoroscope described in claim 1, wherein the non-demagnifying image intensifier comprises a microchannel plate.

7. The high resolution X-ray fluoroscope described in claim 1, further comprising a fiber optic component intimately optically coupled between the scintillator and the image intensifier.

8. The real-time fluoroscopic system described in claim 1, wherein the optical magnification capability of the video camera is in the range of 10×.

9. A high resolution low dose magnifying X-ray fluoroscopic system, comprising:

a. a moveable frame;

b. an X-ray source mounted to a first portion of the frame; and c. an X-ray fluoroscope mounted to a second portion of the frame such that an X-ray beam from the X-ray source impinges the X-ray fluoroscope, the X-ray fluoroscope comprising:

i. a scintillator;

ii. a non-demagnifying image intensifier mounted with an input in optical contact with the scintillator;

iii. a close-up lens system mounted in optical contact to an output of the image intensifier; and iv. an autofocus video camera having optical zoom magnification capabilities mounted adjacent to an output of the close-up lens.

10. The high resolution low dose X-ray system described in claim 9, further comprising a display unit in communication with the camera for displaying an image generated by the X-ray fluoroscope.

11. The high resolution low dose X-ray system described in claim 9, further comprising a fiber optic plate intimately coupled between the scintillator and the image intensifier.

12. The high resolution low dose X-ray system described in claim 9, wherein the frame is moveable vertically and horizontally.

13. The real-time fluoroscopic system described in claim 9, wherein the optical magnification capability of the video camera is in the range of 10×.

14. A real-time fluoroscopic system for imaging surgical and diagnostic procedures, the system comprising:

a. an X-ray source;

b. an X-ray receptor including a scintillator for converting the X-ray signal to the visible light spectrum;

c. a frame configured to position the X-ray source and the X-ray receptor opposed from one another on opposite sides of a subject undergoing a surgical or diagnostic procedure;

d. a video camera capable of auto focus and optical zoom magnification; and e. a lens system for focusing and transmitting an image from the X-ray receptor to the video camera, the lens system being proximally located therebetween.

15. The real-time fluoroscopic system described in claim 14, wherein the optical magnification capability of the video camera is in the range of 10×.

16. The real-time fluoroscopic system described in claim 14, further comprising a non-demagnifying image intensifier mounted in optical contact between the scintillator of the X-ray receptor and the close-up lens system.

* * * * *